United States Patent
Sievers

(10) Patent No.: US 9,694,124 B2
(45) Date of Patent: Jul. 4, 2017

(54) CARDIAC SUPPORT SYSTEM AND A CARDIAC SUPPORT METHOD

(71) Applicant: University of Luebeck, Luebeck (DE)

(72) Inventor: Hans-Hinrich Sievers, Kronshagen (DE)

(73) Assignee: Universitaet zu Luebeck, Luebeck (DE)

( * ) Notice: Subject to any disclaimer, the term of this patent is extended or adjusted under 35 U.S.C. 154(b) by 52 days.

(21) Appl. No.: 14/899,194

(22) PCT Filed: Jun. 13, 2014

(86) PCT No.: PCT/DE2014/100197
§ 371 (c)(1),
(2) Date: Apr. 7, 2016

(87) PCT Pub. No.: WO2014/202051
PCT Pub. Date: Dec. 24, 2014

(65) Prior Publication Data
US 2016/0213828 A1    Jul. 28, 2016

(30) Foreign Application Priority Data
Jun. 18, 2013    (DE) .................. 10 2013 106 352

(51) Int. Cl.
A61M 1/12 (2006.01)
A61M 1/10 (2006.01)
A61F 2/24 (2006.01)

(52) U.S. Cl.
CPC .............. *A61M 1/122* (2014.02); *A61F 2/24* (2013.01); *A61M 1/1008* (2014.02); *A61M 1/1096* (2014.02)

(58) Field of Classification Search
CPC ................. A61M 1/106; A61M 1/101; A61M 2001/122
(Continued)

(56) References Cited

U.S. PATENT DOCUMENTS

| 4,994,078 A | 2/1991 | Jarvik |
| 6,048,363 A | 4/2000 | Nagyszalanczy |

(Continued)

FOREIGN PATENT DOCUMENTS

| DE | 69531399 T2 | 6/2004 |
| DE | 69730617 T2 | 9/2005 |

(Continued)

OTHER PUBLICATIONS

International Search Report in International Application No. PCT/DE2014/100197, dated Oct. 22, 2014.

*Primary Examiner* — Suzette J Gherbi
(74) *Attorney, Agent, or Firm* — Stephan A. Pendorf; Patent Central LLC

(57) ABSTRACT

A cardiac support system comprising an intake region for the intake of blood, an outlet region for discharging the intake blood, a pump arrangement for conveying the blood from the intake region to the outlet region, a pump-aorta connection, and a suction connection from the intake region to the pump, parts of the function of the heart being taken on by said cardiac support system, and a cardiac support method having the steps of taking in blood from within the left half of the heart, pumping, and transferring aspirated blood into the aorta with the cardiac support system.

15 Claims, 3 Drawing Sheets

(58) Field of Classification Search
USPC .................................................. 623/3.1–3.3
See application file for complete search history.

(56) References Cited

U.S. PATENT DOCUMENTS

| | | | |
|---|---|---|---|
| 8,226,712 | B1 | 7/2012 | Frazier et al. |
| 8,870,951 | B1 * | 10/2014 | Frazier .................. A61M 1/101 |
| | | | 623/3.13 |
| 2002/0128587 | A1 | 9/2002 | Aboul-Hosn et al. |
| 2004/0054251 | A1 | 3/2004 | Liotta |
| 2010/0268334 | A1 * | 10/2010 | Pate ...................... A61M 1/101 |
| | | | 623/3.14 |
| 2014/0207232 | A1 * | 7/2014 | Garrigue ............... A61M 1/101 |
| | | | 623/3.13 |
| 2016/0151552 | A1 * | 6/2016 | Solem .................. A61M 1/1081 |
| | | | 623/3.27 |
| 2016/0199555 | A1 * | 7/2016 | Siegenthaler ............. A61F 2/24 |
| | | | 623/3.13 |
| 2017/0021072 | A1 * | 1/2017 | Forsell ............... B01D 46/0065 |
| 2017/0035569 | A1 * | 2/2017 | Deem ...................... A61F 2/243 |

FOREIGN PATENT DOCUMENTS

| | | | | |
|---|---|---|---|---|
| FR | 2485928 | A1 | | 1/1982 |
| JP | 0768091 | A1 * | 4/1997 | ............ A61M 1/101 |

* cited by examiner

CARDIAC SUPPORT SYSTEM AND A CARDIAC SUPPORT METHOD

The invention relates to a cardiac support system comprising a suction region for drawing in intake blood, an outlet region for discharging the intake blood, a pump arrangement for transporting the blood from the intake region to the outlet region, a pump-aorta connection, and a suction connection from the intake region to the pump, where parts of the heart function are taken over by the cardiac support system.

The invention further relates to cardiac support methods, in particular with a cardiac support system according to the invention, comprising the steps of suctioning blood within the left heart, pumping, and transferring the taken in blood into the aorta.

Heart failure is a pathological inability of the heart to transport the amount of blood required by the body without a pressure rise in the atria. In particular, ventricles which are larger/dilated and thus can not achieve sufficient power to transport the blood any longer, lead this failure.

Treatment of such heart failure with drugs is usually maxed out or beyond treatment after a certain period, whereby the heart failure ultimately has to be assisted by means of a cardiac support system, this cardiac support system to restore the blood transport capacity again.

From the prior art it is known to implant a cardiac support system on the apex of the heart by means of a thumb-sized inlet connection, said inlet connection placed approximately 3 cm deep within the left ventricle. Here, the inlet connection forms a cannula.

From the document DE 695 31 399 T2 a cardiac support system in the form of an artificial heart is known, wherein a pump assembly is disposed within the left ventricle and directs blood from the left ventricle into the aorta through the aortic valve.

DE 697 30 617 T2 shows a circulatory support system that supports or temporarily replaces the pumping function of a patient's heart with an external to the body, portable blood flow pump that regulates cardiac function via a processor-controlled control unit.

The U.S. Pat. Nos. 8,226,712 B1 and 6,048,363 A show an artificial heart with automatic blood flow and pressure regulation, a so-called "TAH system" (Total Artificial Heart) in which the function of the heart is taken over or a so-called LVAD (Left Ventricle Assist Device), in which a pump is connected directly to the left atrium, while a part of the heart, including but not limited to the mitral valve, is bypassed.

U.S. Pat. No. 4,994,078 A shows several types of artificial heart with pumps that do not require flaps and a cardiac support system, which is introduced into the ventricle and is driven as a hydraulic bag by muscle power, to allow the function of the ventricle.

A problem with the current state of the art inlet connection/cannula, is that thrombi develop on the cannula itself as well as behind the mitral valve. The thrombus involves the mechanical relief of the left ventricle, so that the flow in the left ventricle is virtually reduced to zero.

The administration of drugs to reduce blood clotting, anticoagulants, can not prevent the emergence of such hyaline thrombi, so that the forming hyaline thrombi can be carried over into the entire body of the patient, which then cannot be automatically dissolved by the body and ultimately may cause major problems for the patient.

The present invention is based on the object of providing a cardiac support system and a cardiac support method that makes it possible to prevent the problem of thrombosis in the area of the left ventricle when using a cardiac support system, so that the risk of thrombus formation by the cardiac support system is completely ruled out.

This object is achieved with a cardiac support device or ventricular support device according to claim 1 and a cardiac support method or ventricular assist method according to claim 8.

In a first embodiment, the suction area is positioned directly following the mitral valve, wherein in this case the natural mitral valve of the patient remains intact and the connection is made by suture via a special prosthesis on the chamber side of the mitral valve.

In a second alternative, the intake/suctioning area is designed as an artificial mitral valve and replaces the simple artificial mitral valve, or the no longer sufficiently functioning natural mitral valve of the patient.

Both alternatives have in common that the blood to be suctioned in normal operation is taken exclusively from the left atrium, which in this regard means that the heart assist system is placed in and on the heart. As a result, the blood is suctioned out of the left atrium and passed through the left ventricle, so that the left ventricle is practically without function. Thrombi can no longer enter into the Ventricular Assist System, resulting in a significant improvement of the clinical problem.

Contrary to the previous belief that the left ventricle could possibly recover, so that the heart support system could be explanted again under certain circumstances, this is however completely impossible in the case of a no longer functional "burnt" left ventricle. As a preliminary step it can already be clearly determined whether a ventricle can at all have the opportunity to recover, or whether, alternatively, the present inventive cardiac assist system and ventricular assist method of the invention is indicated.

The suction connection is available in the variant wherein the natural mitral valve of the patient is replaced, or an artificial mitral valve is already in place, having an inlet connection of the pump assembly and a thereon arranged mitral apical connector, wherein at the pump far end an artificial mitral valve is arranged, wherein the artificial mitral valve can be located in the area of the natural mitral valve of the left ventricle.

As an alternative, in the case of a well-preserved and functioning mitral valve, the suction connection is comprised of an inlet connection [drive support] of the pump assembly and a thereon arranged mitral apical connector, wherein on the end distant from the pump a mitral valve implant is arranged, wherein the mitral valve implant can be provided under standard conditions at the mitral valve annulus of the left ventricle.

The suction area and the suction connection are in normal conditions provided within the left chamber/ventricle. The left ventricle is converted to virtually no function.

The pump-aorta connection is intended to be provided outside of the left ventricle, as in this way a good blood flow is realized and the pump assembly can be easily configured accordingly.

The outlet is intended to be provided within the aorta so that the aspirated blood from the left atrium can be introduced directly into the aorta, bypassing the aortic valve.

Preferably, an additional cannula can be provided between the left ventricle and the right atrium, in the case that an overpressure should be formed in the now inoperative left ventricle and this is not cleaned even by the aortic valve.

The suction connection has, at least in sections, at least on the inside, a spiral-shaped wall, wherein a transport of the blood in the pumping direction is supported. In this particular configuration, it is possible to support the blood transport.

The spiral-shaped wall of the suction connection is supported with a geometric structuring, especially through ridges, tracks, conduits, guide walls, indentations and/or bulges of the inner wall for an acceleration of the blood in blood transport direction.

Preferably the configuration of the inner wall of the suction connection is configured with a spiral shape in the direction of the blood transport structure for an acceleration of the blood transport in the suction connection.

The suction is formed integrally.

The suction connection includes a sensor for detecting the flow velocity, flow acceleration and/or the blood flow, wherein the sensor system can be connected with the pump arrangement for transporting the blood.

The pump arrangement for transporting the blood includes a control unit which is connected to the sensor.

The inventive cardiac assist method is characterized by the suctioning of the blood immediately after the mitral valve, whereby this is carried out such that the blood is taken from the left atrium.

The blood is transported exclusively by suctioning the blood from the left atrium, bypassing the left ventricle and introducing the aspirated blood into the aorta.

An over-pressurization forming within the left ventricle can be drained into the right atrium.

An exemplary embodiment of the invention will be described in detail with reference to the accompanying drawings.

Therein:

Figure 1:
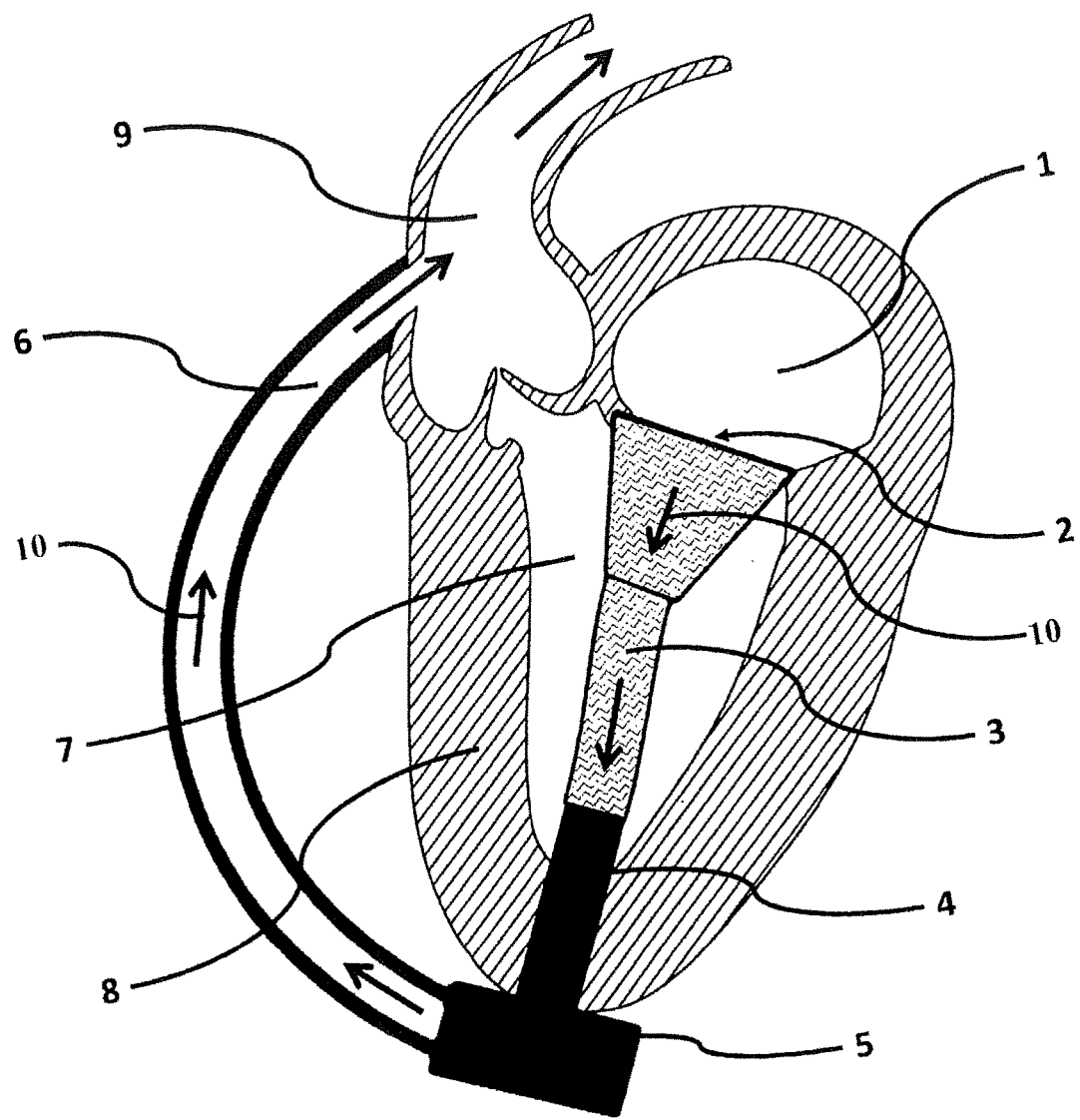
FIG. 1 is a schematic representation of a first embodiment of the cardiac assist system of the invention.

In FIG. 1 a schematic representation of a first embodiment of the cardiac assist system of the invention is illustrated.

The illustrated portion of the heart consists of the left atrium 1, the left ventricle/left heart chamber 7, the aorta 9 as well as the aortic valve disposed between the left ventricle 7 and the aorta 9 and the mitral flap area 2 between the left atrium 1 and the left ventricle 7.

The cardiac support system according to the invention comprises a pump 5, a pump-aorta connection 6, which connects the pump to the aorta 9, so that the blood in the aorta 9 can be promoted in the direction of blood flow 10.

Further, the cardiac support system according to the invention comprises drive assembly connector at the pump 5, a suction connection 4, at the end of which remote from the pump a mitral apical connector 3 is arranged. At the mitral apical connector 3, at the end remote from the pump, an artificial mitral valve 2 is disposed.

According to the invention, blood is suctioned from the left atrium 1 through the artificial mitral valve 2 through in the mitral apical connector 3 and promoted in blood flow direction 10 by the pump 5 through the pump-aorta connection 6 into the aorta 9. Here, the left ventricle 7 is completely bypassed.

Figure 2:
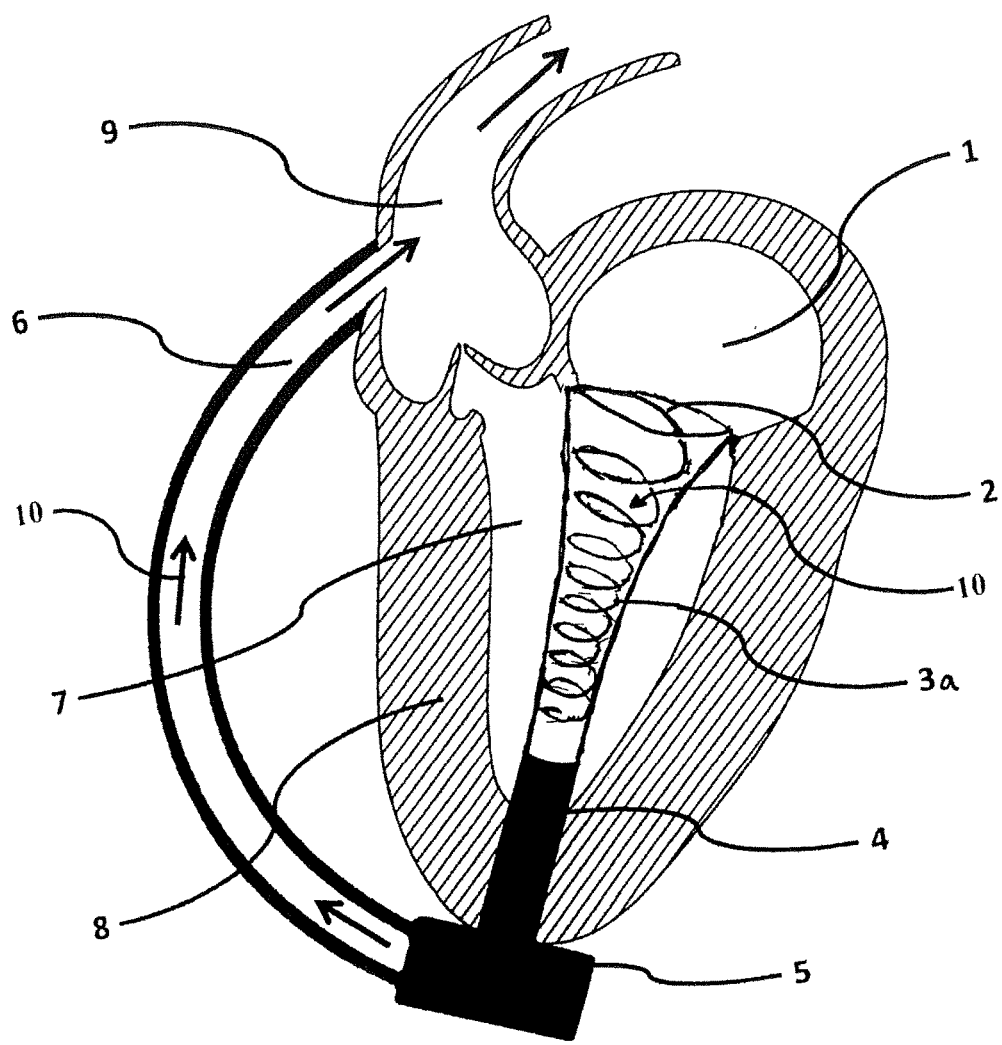
FIG. 2 is a schematic representation of a second embodiment of the cardiac assist system according to the invention and FIG. 3 is a schematic representation of a third embodiment of the cardiac assist system of the invention with control unit.

Next, two other embodiments are explained, reference being made to the description of FIG. 1 for the general function of the individual elements, In FIG. 2 a schematic representation of a second embodiment of the cardiac assist system of the invention is illustrated.

The suction connection 2, 3, 4 is made in one piece and on the inner wall a spiral geometry 3a, for example, as topography, is provided to orient and possibly accelerate the flow of blood.

Figure 3:
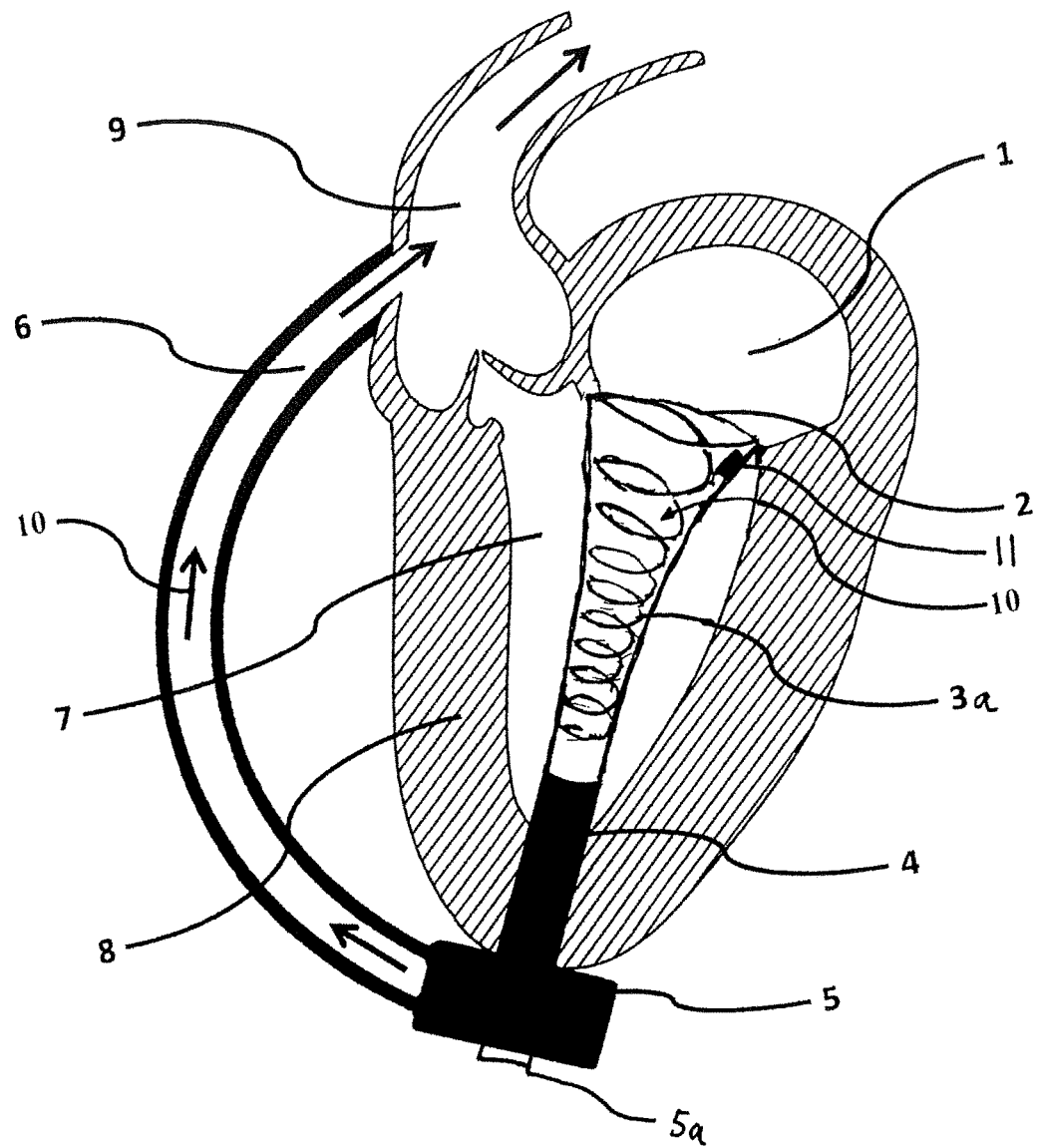

FIG. 3 shows a schematic representation of a third embodiment of the cardiac assist system of the invention with a control unit.

So that the pump assembly 5 can control and individually optimize the flow of blood and/or blood demand, unit 5a controls the pump assembly 5, for which purpose the signals of the sensor system 11 are used, collected, evaluated and stored and/or preferably also transmitted.

The power supply of the pump assembly as well as the other active components is preferably carried out autonomously, for example, via thermal generators via the body, batteries and/or a proximal wireless power transmission method.

LIST OF REFERENCE NUMBERS

1 left atrium
2 mitral valve
3 mitral apical connector
3a spiral inner wall/geometry
4 pump socket, suction connection
5 pump
5a control unit
6 pump-aorta connection
6a outlet
7 left ventricle
8 ventricular wall
9 aorta
10 blood flow direction
11 sensors

The invention claimed is:

1. A cardiac support system comprising
a suction area for aspiration of blood,
an outlet area (6a) for discharging aspirated blood,
a pump arrangement (5) for transporting the aspirated blood from the suction area to the outlet area (6a),
a pump-aorta connection (6), provided outside of the left ventricle (7), and
a suction connection (4) between the suction area and the pump,
wherein portions of the cardiac function are taken over by the cardiac support system,
wherein
the suction area is arranged immediately after an artificial mitral valve (2)
or
the suction area is designed as an artificial mitral valve (2), and
wherein in each case the blood to be aspirated is taken from the left atrium (1).

2. The cardiac support system according to claim 1, wherein the suction connection (4, 3, 2) is comprised of a pump socket (4) of the pump assembly and arranged thereon a mitral apical connector (3), wherein an artificial mitral valve (2) is disposed at the pump-distant end of the mitral apical connector (3), and wherein the artificial mitral valve (2) is intended to be locatable in the area of a natural mitral valve of the left ventricle (7).

3. The cardiac assist system according to claim 1, wherein the suction connection (4, 3) is comprised of a pump socket (4) of the pump assembly and an arranged thereon mitral apical connector (3), wherein on the pump far end of the mitral apical connector (3) an artificial mitral valve is provided, and said the artificial mitral valve is provided arranged on a mitral valve annulus of the left ventricle (7).

4. The cardiac assist system according to claim 1, wherein the suction area and the suction connection (4, 3) are introduced within the left ventricle (7).

5. The cardiac assist system according to claim 1, wherein an outlet (6a) is provided when in use within the aorta (9).

6. The cardiac assist system according claim 1, wherein in use a cannula is provided between the left ventricle (7) and the right atrium.

7. The cardiac assist system according to claim 1, wherein the suction connection (4, 3, 2) has, at least in sections, an at least internally spiral-shaped wall (3a), assisting the pump in the blood transport direction (10).

8. The cardiac support system according to claim 7, wherein the spiral-shaped wall of the suction connection (3a) supports an acceleration of the blood in the blood transport direction (10) via a geometrical structure.

9. The cardiac assist system according to claim 1, wherein the suction connection (4, 3, 2) is constructed in one piece.

10. The cardiac assist system according to claim 1, wherein the suction connection (4, 3, 2) includes a sensor (11) for detecting the flow rate, flow acceleration and/or of blood flow, wherein the sensor (11) can be connected with the pump (5) for transport of the blood.

11. The cardiac support system according to claim 10, wherein the pump (5), for transport of the blood, includes a control unit (5a), which is connectable to the sensor (11).

12. The cardiac assist method for a cardiac assist system according to claim 1, comprising the steps of:
suctioning of blood from within the left half of the heart,
pumping and transporting the aspirated blood into the aorta (9), wherein
the suctioning is carried out immediately after the aspiration of the blood from the mitral valve (2) such that the blood is removed from the left atrium (1).

13. The cardiac support method according to claim 12, wherein a transport of blood is carried out exclusively by suctioning the blood from the left atrium (1), bypassing the left ventricle (7), and introducing the aspirated blood into the aorta (9).

14. The cardiac assist method according to claim 12, wherein an over-pressure forming within the left ventricle (7) is diverted into the right atrium.

15. The cardiac support system according to claim 7, wherein the spiral-shaped wall of the suction connection (3a) supports an acceleration of the blood in the blood transport direction (10) via a geometrical structure selected from the group consisting of projections, tracks, guide channels, guide walls, and grooves.

\* \* \* \* \*